United States Patent [19]

Fürst et al.

[11] Patent Number: 4,568,491

[45] Date of Patent: Feb. 4, 1986

[54] PROCESS FOR THE PREPARATION OF CHOLESTEROL DERIVATIVES AND NOVEL INTERMEDIATES THEREFOR

[75] Inventors: Andor Fürst, Basel; Ludwig Labler, Allschwil; Werner Meier, Bottmingen, all of Switzerland

[73] Assignee: Hoffmann-La Roche Inc., Nutley, N.J.

[21] Appl. No.: 584,200

[22] Filed: Feb. 27, 1984

Related U.S. Application Data

[63] Continuation of Ser. No. 364,383, Apr. 1, 1982, abandoned.

[30] Foreign Application Priority Data

Apr. 29, 1981 [CH] Switzerland .......................... 2784/81

[51] Int. Cl.[4] ................................................ C07J 5/00
[52] U.S. Cl. .......................... 260/239.55 R; 260/397.5; 260/239.55 D; 260/397.2
[58] Field of Search ................... 260/239.55 D, 397.5, 260/239.55 R

[56] References Cited

U.S. PATENT DOCUMENTS

| 3,994,878 | 11/1976 | Partridge, Jr. et al. ... 260/239.55 D |
| 4,021,423 | 5/1977 | Baggiolini et al. ........ 260/239.55 D |
| 4,026,882 | 5/1977 | Baggiolini et al. ........ 260/239.55 D |
| 4,028,349 | 6/1977 | Partridge, Jr. et al. ... 260/239.55 D |
| 4,038,272 | 7/1977 | Partridge, Jr. et al. ... 260/239.55 D |
| 4,268,453 | 5/1981 | Barner et al. .................... 260/397.5 |

FOREIGN PATENT DOCUMENTS 45254 5/1981 European Pat. Off. ... 260/239.55 R

Primary Examiner—Elbert L. Roberts
Attorney, Agent, or Firm—Jon S. Saxe; Bernard S. Leon; George W. Johnston

[57] ABSTRACT

The invention is concerned with a process for the preparation of 1 hydrogen or hydroxy cholesterol derivatives and intermediates therefor. The compounds of the present invention are useful as intermediates in the preparation of 24,25-dihydroxy and 1α, 24,25-trihydroxy-cholecalciferol.

5 Claims, No Drawings

PROCESS FOR THE PREPARATION OF CHOLESTEROL DERIVATIVES AND NOVEL INTERMEDIATES THEREFOR

This is a continuation of application Ser. No. 364,383 filed Apr. 1, 1982 now abandoned.

DESCRIPTION OF THE INVENTION

This process comprises (a) reacting a pregnane derivative of the formula

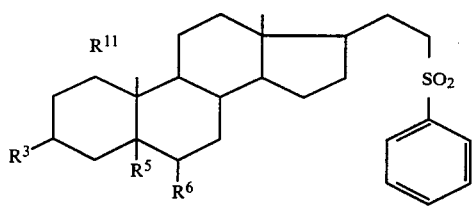

II wherein $R^{11}$ is hydrogen, $R^3$ and $R^5$ together are a 3α,5-bond and $R^6$ is $C_{1-4}$-alkoxy, or $R^{11}$ is hydrogen or a readily-cleavable etherified hydroxy group, $R^3$ is a readily-cleavable etherified hydroxy group and $R^5$ and $R^6$ together are a C—C bond, with a compound of the formula

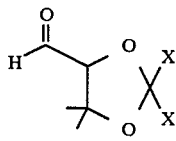

III wherein X is hydrogen or methyl, (b) reductively eliminating the β-hydroxysulphonyl grouping from the resulting compound of the formula

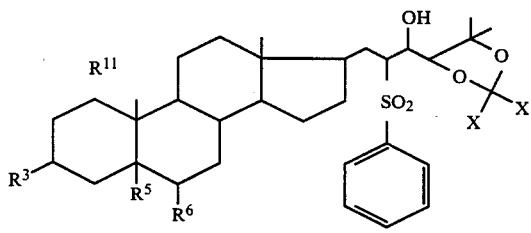

IV wherein X, $R^{11}$, $R^3$, $R^5$ and $R^6$ are as above, (c) catalytically hydrogenating the resulting compound of the formula

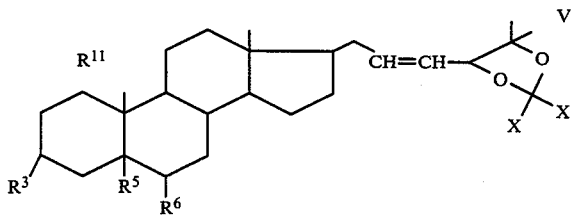

V wherein X, $R^{11}$, $R^3$, $R^5$ and $R^6$ are as above, (d) hydrolyzing the resulting compound of the formula

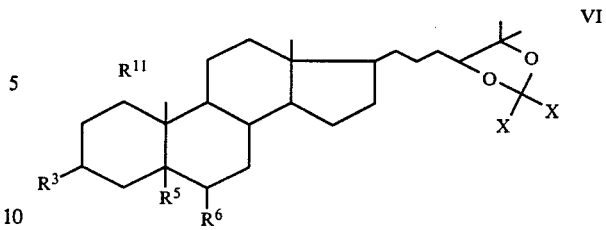

VI wherein X, $R^{11}$, $R^3$, $R^5$ and $R^6$ are as above, to a compound of the formula

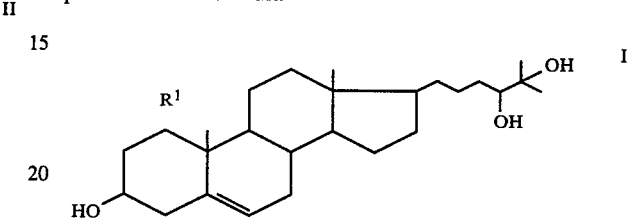

I wherein $R^1$ is hydrogen or hydroxy, and (e) if desired, separating a resulting diastereomeric mixture of compounds of formula I.

The compounds of formula I are known intermediates in the preparation of the vitamin $D_3$ derivatives 24,25-dihydroxy- and 1α,24,25-trihydroxycholecalciferol and can be converted into these in a known manner (see DOS No. 2 710 062) or in analogy thereto.

Examples of $C_{1-4}$-alkoxy groups are methoxy, ethoxy, n-propoxy, isopropoxy and butoxy, preferably methoxy. Ether groups $R^{11}$ or $R^3$ which can be readily cleaved, i.e., without affecting other positions in the molecule, are preferably groups of the formula R'O—C(R,R")—O— in which R is hydrogen or $C_{1-4}$-alkyl and R' and R" are $C_{1-4}$-alkyl or R' and R" together are $C_{3-6}$-alkylene. Especially-preferred ether groups are tetrahydro-2H-pyran-2-yloxy and 1-ethoxyethoxy.

In order to prepare the 24R-diastereomers of formula I, there is preferably used as the starting material a compound of formula III in which X is methyl, especially (S)-2,2,5,5-tetramethyl-1,3-dioxolane-4-carboxaldehyde. The starting material can, however, also be (RS)-2,2,5,5-tetramethyl-1,3-dioxolane-4-carboxaldehyde in which case the obtained mixture of 24R- and 24S-diastereomers of formula I must be separated into the diastereomers.

For the reaction of a compound of formula II with a compound of formula III, the compound of formula II is conveniently first converted into the magnesium or lithium salt with a $C_{1-4}$-alkylmagnesium halide such as methylmagnesium bromide or with a $C_{1-4}$-alkyl lithium such as butyl lithium in an inert solvent such as a hydrocarbon, for example, benzene or toluene, or an ether, for example, tetrahydrofuran. The preparation of the magnesium salt is conveniently carried out while heating, preferably by boiling under reflux, and the preparation of the lithium salt is conveniently carried out at temperatures below −20° C., preferably at −75° C. The temperature at which the subsequent reaction with the aldehyde of formula III is carried out is not critical when the magnesium salt is used; the reaction is preferably carried out at room temperature. When the lithium salt is used, the reaction is conveniently carried out at −20° C. to room temperature.

Step (b) of the process can be carried out with the addition product of formula IV. The yield of C(22)-olefin of formula V is, however, higher when the addition product is first transformed into an n-$C_{1-4}$-alkanoylate such as the formate, acetate, n-propionate or n-butyrate or a sulphonate such as the mesylate or a thiolate such as the thioacetate and then the β-acyloxysulphonyl grouping is reductively eliminated from the resulting ester. Since the C(23)-hydroxy group of certain isomers of formula IV is sterically hindered, energetic reaction conditions are necessary depending on the acylating agent used. For the acetylation, for example, there is indicated a treatment with acetic anhydride in triethylamine or pyridine in the presence of 4-dimethylaminopyridine, conveniently under reflux. The reduction of the resulting acylate can be carried out using an alkali metal amalgam such as sodium amalgam in a solvent such as a $C_{1-4}$-alkanol, for example, methanol, if desired in the presence of an ether, for example, tetrahydrofuran, or of ethyl acetate as the cosolvent, at a temperature up to $-10°$ C., preferably at room temperature.

The catalytic hydrogenation of the compounds of formula V can be carried out using Raney nickel or using platinum or palladium-on-carbon in a solvent such as a $C_{1-4}$-alkanol, for example, ethanol, or an ether, for example, tetrahydrofuran. The hydrogenation medium is held slightly alkaline to neutral by the addition of a base such as an alkali metal bicarbonate, for example, sodium bicarbonate, or a tertiary amine, for example, triethylamine. The temperature and the pressure are not critical. However, the catalytic hydrogenation is preferably carried out at room temperature and normal pressure.

The hydrolysis of a compound of formula VI to a compound of formula I can be carried out by treatment with an acid in a solvolytic medium. As the solvolytic medium, there come into consideration aqueous media which contain a miscible cosolvent. Suitable cosolvents are ethereal solvents such as dioxan or tetrahydrofuran, ketones such as acetone and methyl ethyl ketone or alcohols such as ethanol. As acids, there come into consideration mineral acids such as hydrochloric acid, hydrobromic acid or sulphuric acid or organic sulphonic acids such as p-toluenesulphonic acid or benzenesulphonic acid. The hydrolysis is conveniently carried out at an elevated temperature, for example, at about 40° C. to 120° C., preferably at about 80° C.

The separation of a thus-obtained diastereomeric mixture of compounds of formula I can conveniently be carried out via ester derivatives, for example, the triacetate or tetraacetate, using chromatographic methods. The complete acetylation of a compound of formula I can be carried out in analogy to the acetylation of the compounds of formula IV described above. The separation of the aformentioned ester derivatives can be carried out in a manner known per se; for example, by thin layer and column chromatography.

The compounds of formulas II, III and V are also objects of the present invention.

The sulphones of formula II in which $R^3$ and $R^5$ together represent a 3α,5-bond, i.e., compounds of the formula

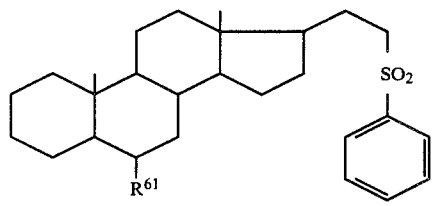

IIa wherein $R^{61}$ is $C_{1-4}$-alkoxy, can be prepared by reacting a corresponding iodide of the formula

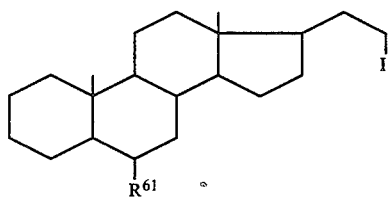

VII wherein $R^{61}$ has the above significance, with sodium benzenesulphinate in dimethylformamide.

Sulphones of the formula

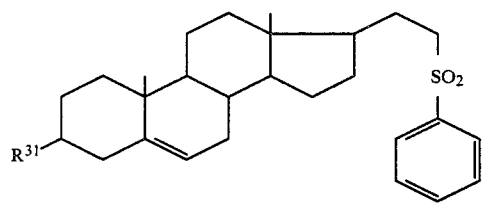

IIb wherein $R^{31}$ is a readily-cleavable etherified hydroxy group, can be prepared, for example, by the retro-i-steroid rearrangement of a sulphone of formula IIa using an acid, in analogy to the hydrolysis of a compound of formula VI to a compound of formula I described above, and subsequent etherification.

The diethers of formula II, i.e., the compounds of the formula

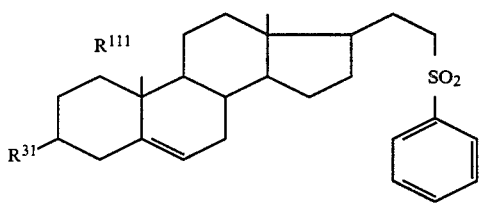

IIc wherein $R^{111}$ and $R^{31}$ are readily-cleavable etherified hydroxy groups, can be prepared by heating (20S)-1α,3β-diacetoxy-20-methyl-21-p-toluenesulphonyloxy-pregn-5-ene with sodium iodide in dimethylformamide, reacting the resulting (20S)-1α,3β-diacetoxy-21-iodo-20-methyl-pregn-5-ene with sodium benzenesulphinate in dimethylformamide, reductively deacetylating the resulting (20S)-1α,3β-diacetoxy-20-methyl-21-phenylsulphonyloxy-pregn-5-ene (for example, with lithium aluminum hydride) and etherifying the resulting (20S)-

1α,3β-dihydroxy-20-methyl-21-phenylsulphonyl-pregn-5-ene.

The compounds of formula III in the R- or S-form and as the racemate can be prepared in the following manner or in analogy thereto:

Methyl (R)-2,2-dimethyl-1,3-dioxane-4-carboxylate is converted with methylmagnesium bromide into (R)-α,α,2,2-tetramethyl-1,3-dioxane-4-methanol, the latter is hydrolyzed with an acid (for example, p-toluenesulphonic acid) to (R)-3-methyl-1,2,3-butanetriol, this is converted (for example, with pivalic acid chloride in pyridine) into (R)-(2,3-dihydroxy-3-methylbutyl)-pivalate, this is acetalyzed with acetone to (R)-(2,2,5,5-tetramethyl-1,3-dioxolan-4-yl)-methylpivalate and the latter is saponified (for example, with alkali) to (R)-2,2,5,5-tetramethyl-1,3-dioxolane-4-methanol. This compound can also be prepared by trans-acetalyzing (R)-α,α,2,2-tetramethyl-1,3-dioxolane-4-methanol in the presence of p-toluenesulphonic acid. The resulting (R)-2,2,5,5-tetramethyl-1,3-dioxolane-4-methanol can then be oxidized (for example, with pyridinium chloroacetate) to (S)-2,2,5,5-tetramethyl-1,3-dioxolane-4-carboxaldehyde.

Further, (RS)-3-methyl-1,2,3-butanetriol, which can be prepared from β,β-dimethylacrylic acid via (RS)-2,3-dihydroxy-3-methylbutyric acid in accordance with the procedure described in Acta Chem. Scand. 23 (1969) 967, can be transformed with benzyl bromide and a base into (RS)-1-benzyloxy-3-methyl-2,3-butanediol, this can be acetalyzed to (RS)-5-benzyloxymethyl-2,2,4,4-tetramethyl-1,3-dioxolane, and this can be hydrogenolyzed to (RS)-2,2,5,5-tetramethyl-1,3-dioxolane-4-methanol. The latter can also be prepared from (RS)-3-methyl-1,2,3-butanetriol via (RS)-(2,3-dihydroxy-3-methylbutyl)-pivalate and (RS)-(2,2,5,5-tetramethyl-1,3-dioxolan-4-yl)-methylpivalate in analogy to the procedure described above in the (R)-series. Alternatively, (RS)-2,2,5,5-tetramethyl-1,3-dioxolane-4-methanol can be prepared by reacting (RS)-3-methyl-1,2,3-butanetriol with acetone and p-toluenesulphonic acid to give a mixture of (RS)-α,α,2,2-tetramethyl-1,3-dioxolane-4-methanol and (RS)-2,2,5,5-tetramethyl-1,3-dioxolane-4-methanol which can be separated by distillation. As described above in the (R)-series, (RS)-2,2,5,5-tetramethyl-1,3-dioxolane-4-methanol can be oxidized to (RS)-2,2,5,5-tetramethyl-1,3-dioxolane-4-carboxaldehyde.

The following Examples illustrate the present invention:

EXAMPLE 1

(a)
(22RS,23RS,24R)-23-Hydroxy-24,25-isopropylidenedioxy-6β-methoxy-22-phenylsulphonyl-3α,5-cyclo-5α-cholestane A solution of 5.0 g (10.6 mmol) of (20S)-6β-methoxy-20-methyl-21-phenylsulphonyl-3α,5-cyclo-5α-pregnane in 95 ml of benzene is treated with 3.44 ml of 3.4M ethereal methylmagnesium bromide solution (11.68 mmol). Solvent is distilled off from the mixture up to a boiling temperature of 77°–78° and the residue is heated under reflux for 7 hours. After cooling to room temperature, 2.016 g (12.7 mmol) of (S)-2,2,5,5-tetramethyl-1,3-dioxolane-4-carboxaldehyde are added thereto. After stirring for 30 minutes at room temperature, the mixture is poured into a mixture of 100 ml of saturated ammonium chloride solution and 100 g of ice and the organic phase is separated. The latter gives, after washing with saturated sodium chloride solution, drying over sodium sulphate and evaporation at 30°/11 Torr, 6.46 g of a colourless resin.

(b)
(22RS,23RS,24R)-23-Acetoxy-24,25-isopropylidenedioxy-6β-methoxy-22-phenylsulphonyl-3α,5-cyclo-5α-cholestane A solution of the product (6.46 g) obtained in paragraph (a) in 104 ml of triethylamine is treated with 12.5 ml of acetic anhydride and 2.1 g of 4-dimethylaminopyridine and the mixture is heated under reflux for 3 hours. The cooled solution is poured into a mixture of 200 ml of saturated sodium hydrogen carbonate solution and 100 g of ice and extracted with ether. The extract is washed with saturated sodium chloride solution, dried over sodium sulphate and evaporated at 30°/11 Torr. The residue is dissolved in 400 ml of toluene and evaporated at 40°/11 Torr. The residual brown oil is filtered in ether solution over a column of 170 g of silica gel and back-washed with ether. After evaporation of the filtrate at 30°/11 Torr, there are obtained 6.46 g of a yellow resin.

(c)
(24R)-24,25-Isopropylidenedioxy-6β-methoxy-3α,5-cyclo-5α-cholest-22(EZ)-ene

A solution of the product (6.46 g) obtained in paragraph (b) in a mixture of 100 ml of methanol and 50 ml of ethyl acetate is treated with 15.2 g of 5% sodium amalgam. After stirring for 1 hour at room temperature, a further 15.2 g of the amalgam are added thereto and after a further 1 hour another 15.2 g of the amalgam are added thereto. Finally, the mixture is stirred for a further 3 hours. The supernatant solution is evaporated at 30°/11 Torr and the evaporation residue is treated with ether and water. The ethereal phase is washed with saturated sodium chloride solution, dried over sodium sulphate and evaporated at 30°/11 Torr. The residue gives, after chromatography on 150 g of silica gel with hexane/ether (19:1), 3.0 g of product of the isomer composition E/Z=3:1 ($^1$H-NMR) in the form of a colourless resin.

(d)
(24R)-24,25-Isopropylidenedioxy-6β-methoxy-3α,5-cyclo-5α-cholestane

A suspension prepared from 8 ml of ethanolic Raney-nickel concentrate and 107 ml of ethanol is shaken for 4 hours in a hydrogen atmosphere. A solution of 2.9 g of the product obtained in paragraph (c) in 58 ml of ethanol as well as 1.16 g of sodium hydrogen carbonate are added thereto. Then, the mixture is shaken for 24 hours in a hydrogen atmosphere. The suspension is suction filtered and the filtrate is evaporated at 40°/11 Torr, there being obtained 2.78 g of product of melting point 108°–110°. After recrystallization from methanol, this product melts at 111°–112°; $[\alpha]^{20}_D = +43.1°$ (c=0.7 in CHCl$_3$).

(e) (24R)-3β,24,25-Trihydroxy-cholest-5-ene

A solution of 2.28 g of the product obtained in paragraph (d) in 23 ml of dioxan is treated with 0.165 g of p-toluenesulphonic acid monohydrate and heated to 80°. 40 ml of water are added dropwise during 10 minutes and the solution is left at 80° for 4 hours. After cooling, 46 ml of water are added dropwise thereto, the separated product is filtered off under suction, washed with water and dried, there being obtained 1.896 g of crude product of melting point 195°–199°. After recrystallization from methanol, the compound melts at 202°–204°; $[\alpha]^{20}_D = -9.8°$ (c=1.0 in $CH_3OH$).

(f) (24R)-3β,24,25-Triacetoxy-cholest-5-ene

A solution of 1.0 g of the crude product obtained in paragraph (e) in 10 ml of triethylamine is treated with 1.8 ml of acetic anhydride and 0.2 g of 4-dimethylaminopyridine and the mixture is heated under reflux for 3 hours. The solution is worked-up in analogy to the procedure described in paragraph (b). The crystalline residue obtained after the toluene treatment yields, by chromatography on 50 g of silica gel with hexane/ether (9:1 and 4:1), 1.131 g of product of melting point 120°–121°. After recrystallization from diisopropyl ether, this product melts at 122°–123°; $[\alpha]^{20}_D = -28.1°$ (c=1.0 in $CHCl_3$).

EXAMPLE 2

(a) (22RS,23RS,24R)-23-Hydroxy-24,25-isopropylidenedioxy-22-phenylsulphonyl-3β-(tetrahydro-2H-pyran-2-yl)-oxy-cholest-5-ene 5.74 g (10.62 mmol) of (20S)-20-methyl-21-phenylsulphonyl-3β-(tetrahydro-2H-pyran-2-yl)-oxy-pregn-5-ene give 7.87 g of product in analogy to Example 1(a).

(b) (22RS,23RS,24R)-23-Acetoxy-24,25-isopropylidenedioxy-22-phenylsulphonyl-3β-(tetrahydro-2H-pyran-2-yl)-oxy-cholest-5-ene The product obtained in paragraph (a) gives 7.79 g of acetylation product in analogy to Example 1(b).

(c) (24R)-24,25-Isopropylidenedioxy-3β-(tetrahydro-2H-pyran-2-yl)-oxy-cholesta-5,22(EZ)-diene The product obtained in paragraph (b) is dissolved in a mixture of 168 ml of methanol and 54 ml of ethyl acetate and, in analogy to Example 1(c), reduced with three 16.6 g portions of 5% sodium amalgam and worked-up. The crude product gives, after chromatography on 150 g of silica gel with hexane/ether (9:1), 3.145 g of product in the form of the E/Z mixture of melting point 158°–160°; $[\alpha]^{20}_D = -53.5°$ (c=1.0 in $CHCl_3$). Two-fold recrystallization from methanol containing a trace of pyridine yields pure 22E-compound of melting point 172°–173°; $[\alpha]^{20}_D = -51.2°$ (c=1.0 in $CHCl_3$).

(d) (24R)-24,25-Isopropylidenedioxy-3β-(tetrahydro-2H-pyran-2-yl)-oxy-cholest-5-ene 2.21 g of the E/Z mixture obtained in paragraph (c) give 2.2 g of product of melting point 112°–116° in analogy to Example 1(d).

(e) (24R)-3β,24,25-Trihydroxy-cholest-5-ene

A solution of 1.9 g of the product obtained in paragraph (d) in 19 ml of dioxan is treated with 0.138 g of p-toluenesulphonic acid monohydrate, heated to 80° and, after the dropwise addition of 8.3 ml of water, left at 80° for 3 hours. After cooling, 38 ml of water are added dropwise thereto, the separated product is filtered off under suction, washed with water and dried, there being obtained 1.52 g of a white powder.

(f) (24R)-3β,24,25-Triacetoxy-cholest-5-ene 0.82 g of the product obtained in paragraph (e) gives in analogy to Example 1(f) 0.527 g of product of melting point 118°–119° which, after recrystallization from diisopropyl ether, melts at 121°–122°; $[\alpha]^{20}_D = -26.0°$ (c=0.5 in $CHCl_3$).

EXAMPLE 3

(a) (22RS,23RS,24RS)-23-Hydroxy-24,25-isopropylidenedioxy-6β-methoxy-22-phenylsulphonyl-3α,5-cyclo-5α-cholestane 5.0 g (10.6 mmol) of (20S)-6β-methoxy-20-methyl-21-phenylsulphonyl-3α,5-cyclo-5α-pregnane give 6.94 g of product in analogy to Example 1(a) using racemic 2,2,5,5-tetramethyl-1,3-dioxolane-4-carboxaldehyde.

(b) (22RS,23RS,24RS)-23-Acetoxy-24,25-isopropylidenedioxy-6β-methoxy-22-phenylsulphonyl-3α,5-cyclo-5α-cholestane The product obtained in paragraph (a) gives 7.0 g of acetylation product in analogy to Example 1(b).

(c) (24RS)-24,25-Isopropylidenedioxy-6β-methoxy-3α,5-cyclo-5α-cholest-22(EZ)-ene The acetylation product obtained in paragraph (b) yields in analogy to Example 1(c) 3.194 g of a resinous mixture of the isomer composition E(24R):R(24S):Z(24R):Z(24S)=4:4:1:1 ($^1$H-NMR).

(d) (24RS)-24,25-Isopropylidenedioxy-6β-methoxy-3α,5-cyclo-5α-cholestane 3.10 g of the mixture obtained in paragraph (c) give in analogy to Example 1(d) 3.09 g of product of melting point 82–84°; $[\alpha]^{20}_D = +44.3°$ (c=1.0 in $CHCl_3$). A sample recrystallized from methanol melts at 89°–91°; $[\alpha]^{20}_D = +45.4°$ (c=1.0 in $CHCl_3$).

(e) (24RS)-3β,24,25-Trihydroxy-cholest-5-ene 2.521 g of the product obtained in paragraph (d) yield in analogy to Example 1(e) 2.043 g of crystalline material of melting point 190°–196°; $[\alpha]^{20}_D = -30.6°$ (c=0.5 in $CH_3OH$).

(f) (24RS)-3β,24,25-Triacetoxy-cholest-5-ene 1.2 g of the crystalline material obtained in paragraph (e) yield 1.342 g of crystalline product of melting point 117°–125° in analogy to Example 1(f).

(g) Chromatographic separation of (24RS)-3β,24,25-triacetoxy-cholest-5-ene

A solution of 1.2 g of the product obtained in paragraph (f) in 40 ml of hexane is added to a column of 100 g of neutral aluminium oxide (activity III) in hexane and, after adsorption has taken place, the column is eluted with hexane/ether (4:1). There is firstly obtained 0.426 g of (24R)-3β,24,25-triacetoxy-cholest-5-ene of melting point 121°–123° which is uniform according to thin-layer chromatography and which melts at 122°–123° after recrystallization from diisopropyl ether; $[\alpha]^{20}_D = -28.8°$ (c=0.5 in $CHCl_3$). After 0.11 g of mixed fraction, there is eluted 0.503 g of (24S)-3β,24,25-triacetoxy-cholest-5-ene of melting point 147°–149° which is uniform according to thin-layer chromatography. After recrystallization, the compound melts at 149°–150°; [α]$^{20}_D$= −38.8° (c=0.5 in CHCl$_3$).

EXAMPLE 4

(a)
(22RS,23RS,24R)-1α,3β-Di-(tetrahydro-2H-pyran-2-yl)-oxy-23-hydroxy-24,25-isopropylidenedioxy-22-phenylsulphonyl-cholest-5-ene 6.80 g (10.62 mmol) of (20S)-1α,3β-di-(tetrahydro-2H-pyran-2-yl)-oxy-20-methyl-21-phenylsulphonyl-pregn-5-ene give 9.26 g of product as a yellowish resin in analogy to example 1(a).

(b)
(22RS,23RS,24R)-23-Acetoxy-1α,3β-di-(tetrahydro-2H-pyran-2-yl)-oxy-24,25-isopropylidenedioxy-22-phenylsulphonyl-cholest-5-ene The product obtained in paragraph (a) gives 8.76 g of acetylation product as a yellowish resin in analogy to Example 1(b).

(c)
(24R)-1α,3β-Di-(tetrahydro-2H-pyran-2-yl)-oxy-24,25-isopropylidenedioxy-cholesta-5,22(EZ)-diene The product obtained in paragraph (b) is reduced with 5% sodium amalgam and worked-up in analogy to Example 1(c). The crude product yields, after chromatography on 230 g of silica gel with hexane/ether (9:1 and 4:1), 3.81 g of product as the E/Z mixture in the form of a yellowish resin.

(d)
(24R)-1α,3β-Di-(tetrahydro-2H-pyran-2-yl)-oxy-24,25-isopropylidenedioxy-cholest-5-ene The product obtained in paragraph (c) is hydrogenated with Raney-nickel in analogy to Example 1(d). The crude product yields, after column chromatography on 120 g of silica gel with hexane/ether (9:1 and 4:1), 3.64 g of product in the form of a white resin.

(e)
(24R)-1α-3β-Dihydroxy-24,25-isopropylidenedioxy-cholest-5-ene

A solution of the product obtained in paragraph (d) in 23 ml of dioxan is treated with 0.16 g of p-toluenesulphonic acid monohydrate, heated to 80° and, after the dropwise addition of 9.6 ml of water, left at 80° for 3 hours. After cooling, 120 ml of water are added dropwise thereto, the separated product is filtered off under suction, washed with water and dried, there being obtained 2.25 g of crude (24R)-1α,3β,24,25-tetrahydroxy-cholest-5-ene of melting point 195°–202°. The product is suspended in 68 ml of acetone and, after the dropwise addition of three drops of 70% perchloric acid, left at room temperature for 30 minutes. The solution is treated with 3.4 ml of triethylamine and evaporated at 30°/11 Torr. The residue gives, after chromatography on 100 g of silica gel with ether and ethyl acetate, 1.66 g of crystalline product which melts at 174°–176° after recrystallization from methanol, [α]$^{20}_D$= −38.4° (c=0.5 in CHCl$_3$).

(f) (24R)-1α,3β,24,25-Tetrahydroxy-cholest-5-ene

A solution of 0.282 g of the product obtained in paragraph (e) in 2.1 ml of dioxan is treated with 0.015 g of p-toluenesulphonic acid monohydrate, heated to 80° and, after the dropwise addition of 0.9 ml of water, left at 80° for 2 hours. After cooling, 10 ml of water are added dropwise thereto, the separated product is filtered off under suction, washed with water and dried, there being obtained 0.219 g of a white powder of melting point 221°–222°.

(g) (24R)-1α,3β,24,25-Tetraacetoxy-cholest-5-ene

A mixture of 0.21 g of the product obtained in paragraph (f), 2.1 ml of triethylamine, 0.38 ml of acetic anhydride and 0.042 g of 4-dimethylaminopyridine is heated under reflux for 3 hours. The solution is worked up in analogy to Example 1(b). The residue, which is dried using 20 ml of toluene, gives, after chromatography on 10 g of silica gel with hexane/ether (4:1), 0.243 g of product as a white resin; [α]$_D^{20}$= −9.4° (c=0.5 in CHCl$_3$).

Preparation of the starting materials:

(1.) (20S)-6β-Methoxy-20-methyl-21-phenylsulphonyl-3α,5-cyclo-5α-pregnane

A mixture prepared by adding 3.43 g of (20S)-21-iodo-6β-methoxy-20-methyl-3α,5-cyclo-5α-pregnane and 2.53 g of sodium benzenesulphinate to 23 ml of dimethylformamide is heated at 80° for 20 minutes. The cooled solution is poured into water and extracted with ether, the extract is washed with water, dried over sodium sulphate and evaporated at 30°/11 Torr. The residue is chromatographed on 100 g of silica gel with hexane/ether (19:1 and 9:1). There is thus obtained as the polar constituent 3.07 g of product which, after recrystallization from ether, melts at 141°–142°; [α]$_D^{20}$= +55.0° (c=0.5 in CHCl$_3$).

(2.) (20S)-20-Methyl-21-phenylsulphonyl-3β-(tetrahydro-2H-pyran-2-yl)-oxy-pregn-5-ene.

(2.1.) (20S)-3β-Hydroxy-20-methyl-21-phenylsulphonyl-pregn-5-ene.

A solution of 1.0 g of (20S)-6β-methoxy-20-methyl-21-phenylsulphonyl-3α,5-cyclo-5α-pregnane in 10 ml of dioxan is treated with 0.080 g of p-toluenesulphonic acid monohydrate and 4.4 ml of water and heated at 80° for 4 hours. The stirred solution is treated with 10 ml of water over a period of 5 minutes and the resulting suspension is suction filtered after cooling to room temperature. The dried residue gives, after chromatography on 60 g of silica gel with methylene chloride/ether (1:1), 0.897 g of product of melting point 198°–199°. A sample recrystallized from methylene chloride/ether melts at 198°–199°; [α]$_D^{20}$= −24.1° (c=0.5 in CHCl$_3$). (2.2.) A suspension of 0.597 g of the product obtained in paragraph 2.1. in 40 ml of benzene is treated with 1.0 ml of 3,4-dihydro-2H-pyran and 0.010 g of anhydrous p-toluenesulphonic acid and the mixture is left at room temperature for 30 minutes. After dilution with ether, the mixture is washed with sodium hydrogen carbonate solution, the organic phase is dried over sodium sulphate and evaporated at 30°/11 Torr. The residue (m.p. 158°–161°) gives, after recrystallization from methylene chloride/ether containing 0.1% triethylamine, 0.601 g of (20S)-20-methyl-21-phenylsulphonyl-3β-(tetrahydro-2H-pyran-2-yl)-oxy-pregn-5-ene of melting point 160°–161°; [α]$_D^{20}$= −25.6° (c=0.56 in CHCl$_3$).

(3.) (20S)-1α,3β-Di-(tetrahydro-2H-pyran-2-yl)-oxy-20-methyl-21-phenylsulphonyl-pregn-5-ene.

(3.1.) (20S)-1α,3β-Diacetoxy-21-iodo-20-methyl-pregn-5-ene.

First process. A mixture prepared by adding 2.34 g of (20S)-1α,3β-diacetoxy-20-methyl-21-p-toluenesulphonyloxy-pregn-5-ene and 1.2 g of sodium iodide to 8 ml of dimethylformamide is heated at 80° for 45 minutes. After cooling to room temperature, the mixture is poured into water and extracted with hexane. The extract is washed with water, dried over sodium sulphate and evaporated at 30°/11 Torr. The residue yields, after chromatography on 35 g of silica gel with hexane/ether (19:1 and 9:1), 1.98 g of product which melts at 136° after recrystallization from pentane; $[\alpha]_D^{20} = -11.0°$ (c=1.0 in CHCl$_3$).

Second process. A solution of 23.4 g of (20S)-1α,3β-diacetoxy-20-methyl-21-p-toluenesulphonyloxy-pregn-5-ene in 260 ml of toluene is treated with 1.04 g of hexadecyl-tri-n-butyl-phosphonium bromide and a solution of 132 g of sodium iodide in 260 ml of water and the mixture is heated under reflux for 5 hours. After cooling, the organic phase is separated, washed with saturated sodium chloride solution, dried over sodium sulphate and evaporated at 30°/11 Torr. Chromatography of the residue on 270 g of silica gel with hexane/ether (19:1 and 9:1) gives 21.1 g of product of melting point 135°-136°. After recrystallization from concentrated pentane solution, there are obtained 16.0 g of product of melting point 136°; $[\alpha]_D^{20} = -11.0°$ (c=1.0 in CHCl$_3$).

(3.2.) (20S)-1α,3β-Diacetoxy-20-methyl-21-phenylsulphonyl-pregn-5-ene.

In analogy to paragraph 1., 21.1 g of the product obtained in paragraph 3.1. are reacted with 13.1 g of sodium benzenesulphinate in 120 ml of dimethylformamide and the solution is worked up to the crude product. Chromatography of the crude product on 300 g of silica gel with hexane/ether (7:3) gives as the polar constituent 16.3 g of product of melting point 104° after recrystallization from ether/hexane; $[\alpha]_D^{20} = -7.4°$ (c=1.0 in CHCl$_3$).

(3.3.) (20S)-1α,3β-Dihydroxy-20-methyl-21-phenylsulphonyl-pregn-5-ene.

A solution of 8.15 g of the product obtained in paragraph 3.2. in 150 ml of tetrahydrofuran is added dropwise while stirring at −20° to a suspension of 3.5 g of lithium aluminium hydride in 250 ml of tetrahydrofuran. After stirring for 2 hours at −20°, 400 ml of ethyl acetate/tetrahydrofuran (1:1) are added dropwise thereto in such a manner that the temperature does not exceed −8°. The mixture obtained is poured into a mixture of 250 ml of 2M potassium sodium tartrate solution and 150 g of ice and extracted with ethyl acetate. The extract is washed with saturated sodium chloride solution, dried over sodium sulphate and evaporated at 30°/11 Torr. There are obtained 6.9 g of product which, after recrystallization from ethyl acetate/methylene chloride, melts at 214°; $[\alpha]_D^{20} = -12.2°$ (c=0.5 in dioxan).

(3.4.) A suspension of 1.71 g of the product obtained in paragraph 3.3. in 75 ml of benzene is treated with 2.0 ml of 3,4-dihydro-2H-pyran and 0.010 g of anhydrous p-toluenesulphonic acid and the mixture is left at room temperature for 2 hours. The solution is washed with saturated sodium hydrogen carbonate solution, dried over sodium sulphate and evaporated at 30°/11 Torr. Chromatography of the residue on 85 g of silica gel with hexane/ether (4:1) yields 1.82 g of (20S)-1α,3β-di-(tetrahydro-2H-pyran-2-yl)-oxy-20-methyl-21-phenylsulphonyl-pregn-5-ene which, after recrystallization from ether/hexane, melts at 150°-152°; $[\alpha]_D^{20} = +12.4°$ (c=1.0 in CHCl$_3$).

(4.) (S)-2,2,5,5-Tetramethyl-1,3-dioxolane-4-carboxaldehyde.

(4.1.) (R)-α,α,2,2-Tetramethyl-1,3-dioxolane-4-methanol.

A solution of 18.9 g of methyl (R)-2,2-dimethyl-1,3-dioxolane-4-carboxylate in 190 ml of ether is added dropwise at 10°-15° while stirring to 120 ml of a 2.95M ethereal solution of methylmagnesium bromide. After stirring for 1.5 hours at room temperature, the mixture is poured into 1 l of saturated ammonium chloride solution, the ethereal phase is separated and the aqueous phase is extracted with ether. The ethereal solutions are dried over sodium sulphate and evaporated at 30°/11 Torr. Chromatography of the residue on 800 g of silica gel with hexane/ether (4:1) gives 15.8 g of product as a colourless oil of boiling point 125°/12 Torr (bulb-tube); $[\alpha]_D^{20} = +17.2°$ (c=2.0 in CHCl$_3$).

(4.2.) (R)-3-Methyl-1,2,3-butanetriol.

A solution of 8.9 g of the product obtained in paragraph 4.1. in 180 ml of 90% aqueous tetrahydrofuran is treated with 0.52 g of p-toluenesulphonic acid monohydrate and the mixture is heated at 70° for 3 hours. After the addition of 4 ml of triethylamine, the mixture is evaporated at 30°/11 Torr, the residue is taken up in benzene and again evaporated to dryness at 11 Torr. Chromatography of the residue on 90 g of silica gel with ethyl acetate and ethyl acetate/tetrahydrofuran (1:1) gives 5.98 g of product as a colourless oil of boiling point 125°/2 Torr (bulb-tube); $[\alpha]_D^{20} = +23.5°$ (c=1.0 in CH$_3$OH).

(4.3.) (R)-(2,3-Dihydroxy-3-methylbutyl)-pivalate.

A solution of 2.87 g of the product obtained in paragraph 4.2. in 15 ml of pyridine is treated at 0° with 2.93 ml of pivalic acid chloride. The mixture is stirred at 0° for 15 minutes and at room temperature for 1.5 hours. The suspension is diluted with 50 ml of ether, suction filtered and the filtrate is evaporated at 30°/11 Torr. After removal of residual amounts of pyridine by dissolution in o-xylene and evaporation at 50°/11 Torr, the residue is chromatographed on 140 g of silica gel with hexane/ether (1:1). There are thus obtained 4.04 g of an oily product; $[\alpha]_D^{20} = +18.2°$ (c=1.0 in CHCl$_3$).

(4.4.) (R)-(2,2,5,5-Tetramethyl-1,3-dioxolan-4-yl)-methylpivalate.

A solution of 3.81 g of the product obtained in paragraph 4.3. in 85 ml of acetone is treated with 0.28 g of anhydrous p-toluenesulphonic acid and left at room temperature for 3 hours. After the addition of 1 ml of triethylamine, the mixture is evaporated at 30°/11 Torr and the residue is chromatographed on 100 g of silica gel with hexane/ether (9:1). There are thus obtained 4.1 g of product as a colourless oil of boiling point 115°/12 Torr (bulb-tube); $[\alpha]_D^{20} = -5.25°$ (c=0.8 in CHCl$_3$).

(4.5.) (R)-2,2,5,5-Tetramethyl-1,3-dioxolane-4-methanol.

(4.5.1.) From (R)-α,α,2,2-tetramethyl-1,3-dioxolane-4-methanol.

A solution of 3.5 g of the product obtained in paragraph 4.1. in 60 ml of acetone is treated with 0.030 g of anhydrous p-toluenesulphonic acid and left at room temperature for 5 days. After the addition of 1 ml of triethylamine, the mixture is evaporated at 30°/11 Torr and the residue is chromatographed on 210 g of neutral aluminium oxide (activity III) with methylene chloride. There is thus obtained, besides 1.81 g of educt, as the polar fraction 0.90 g of product as a colourless oil of boiling point 125°/12 Torr; $[\alpha]_D^{20} = -13.1°$ (c=0.7 in CHCl$_3$).

(4.5.2.) From (R)-(2,2,5,5-tetramethyl-1,3-dioxolan-4-yl)methylpivalate.

A solution of 3.88 g of the product obtained in paragraph 4.4. in 65 ml of 0.5N methanolic sodium hydroxide is left at room temperature for 4 hours and subsequently evaporated at 30°/11 Torr. Chromatography of the residue on 100 g of silica gel with pentane/ether (9:1) gives 2.36 g of product as a colourless oil; $[\alpha]_D^{25} = -15.0°$ (c=1.0 in CHCl$_3$).

(4.6.) (S)-2,2,5,5-Tetramethyl-1,3-dioxolane-4-carboxaldehydehyde.

A solution of 2.0 g of the product obtained in paragraph 4.5.2. in 4 ml of methylene chloride is added at room temperature while stirring to a mixture prepared by adding 12.5 g of anhydrous calcium sulphate and 4.16 g of pyridinium chlorochromate to 25 ml of methylene chloride. After stirring for 70 minutes at room temperature, the mixture is added to a column of 40 g of silica gel prepared in methylene chloride and washed with methylene chloride. The eluates which are uniform according to thin-layer chromatography give, after combination, evaporation of the solvent at 50° and distillation of the residue at 105°/12 Torr (bulb-tube), 1.0 g of product as a colourless oil; $[\alpha]_D^{20} = -138.6°$ (c=1.0 in hexane).

(5.) (RS)-2,2,5,5-Tetramethyl-1,3-dioxolane-4-carboxaldehyde.

(5.1.) (RS)-(2,3-Dihydroxy-3-methylbutyl)-pivalate.

From 3.0 g of (RS)-3-methyl-1,2,3-butanetriol there are obtained, in analogy to paragraph 4.3., 4.42 g of product which melts at 75°-76° after recrystallization from ether.

(5.2.) (RS)-(2,2,5,5-Tetramethyl-1,3-dioxolan-4-yl)-methylpivalate.

From 1.34 g of product obtained in paragraph 5.1. there are obtained, in analogy to paragraph 4.4., 1.46 g of product which melts at 62°-63° after recrystallization from hexane.

(5.3.) (RS)-1-Benzyloxy-3-methyl-2,3-butanediol.

A solution of 0.460 g of sodium in 10 ml of ethanol is treated with 2.4 g of (RS)-3-methyl-1,2,3-butanetriol. 20 ml of toluene are added thereto and, with the simultaneous dropwise addition of 60 ml of toluene, solvent is distilled off slowly until the distillate amounts to 75 ml. The residual suspension is suction filtered, the residue is washed with ether and dried at room temperature/11 Torr. The salt is suspended in 10 ml of tetrahydrofuran, then 0.740 g of tetrabutylammonium iodide and 4.0 ml of benzyl bromide are added and the mixture is stirred at room temperature for 3 days. The mixture is diluted with benzene and concentrated at 30°/11 Torr. The residue is chromatographed on 30 g of silica gel with hexane/ether (4:1). There are thus obtained, besides 0.616 g of (RS)-1,2-dibenzyloxy-3-methyl-3-butanol, as the polar fraction 1.15 g of the desired product as a colourless oil of boiling point 150°/2 Torr (bulb-tube).

(5.4.) (RS)-5-Benzyloxymethyl-2,2,4,4-tetramethyl-1,3-dioxolane.

A solution of 1.15 g of the product obtained in paragraph 5.3. in 100 ml of acetone is treated with 0.050 g of anhydrous p-toluenesulphonic acid and left at room temperature for 16 hours. After the addition of 1 ml of triethylamine, the mixture is evaporated at 30°/11 Torr. Chromatography of the residue on 10 g of silica gel with hexane/ether (4:1) gives 1.34 g of product as an oil of boiling point 150°/2 Torr (bulb-tube).

(5.5.) (RS)-2,2,5,5-Tetramethyl-1,3-dioxolane-4-methanol.

(5.5.1.) From (RS)-(2,2,5,5-tetramethyl-1,3-dioxolan-4-yl)-methylpivalate.

From 0.642 g of the product obtained in paragraph 5.2. there is obtained, in analogy to paragraph 4.5.2., 0.382 g of product as an oil of boiling point 130°/12 Torr (bulb-tube), (5.5.2.) From (RS)-5-benzyloxymethyl-2,2,4,4-tetramethyl-1,3-dioxolane.

0.15 g of the product obtained in paragraph 5.4 is added to a pre-hydrogenated mixture of 0.50 g of 5% palladium-on-carbon, 0.10 g of sodium hydrogen carbonate and 10 ml of ethyl acetate and the mixture is shaken at room temperature in a hydrogen atmosphere. After completion of the uptake of gas, the catalyst is filtered off and the filtrate is evaporated at 30°/11 Torr. The residue gives, after distillation at 130°/12 Torr (bulb-tube), 0.30 g of product as a colourless oil.

(5.5.3.) From (RS)-3-methyl-1,2,3-butanetriol.

A solution of 1.2 g of (RS)-3-methyl-1,2,3-butanetriol in 20 ml of acetone is treated with 0.010 g of anhydrous p-toluenesulphonic acid and left at room temperature for 5 days. After the addition of 0.3 ml of triethylamine, the mixture is evaporated at 30°/11 Torr and the residue is distilled at 130°/11 Torr. The distillate (1.55 g) gives, after chromatography on 90 g of neutral aluminium oxide (activity III) with methylene chloride, as the non-polar fraction 0.81 g of (RS)-$\alpha,\alpha,2,2$-tetramethyl-1,3-dioxolane-4-methanol and as the polar fraction 0.52 g of the desired product.

In a batch carried out in an analogous manner using 12.7 g of educt the crude product is separated by fractional distillation. There are thus obtained 7.1 g of (RS)-$\alpha,\alpha,2,2$-tetramethyl-1,3-dioxolane-4-methanol of boiling point 33°-34°/2 Torr, 0.5 g of mixed fraction (b.p. 34°-38°/2 Torr) and as the residue 5.6 g of the desired product.

(5.6.) (RS)-2,2,5,5-Tetramethyl-1,3-dioxolane-4-carboxaldehyde.

4.0 g of the product obtained in paragraph 5.5.3. give, in analogy to paragraph 4.6., 2.38 g of product as a colourless oil of boiling point 105°/12 Torr.

What is claimed is:

1. A pregnane derivative of the formula

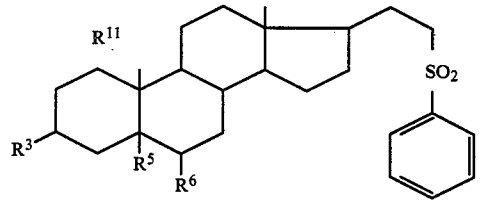

II wherein $R^{11}$ is hydrogen, $R^3$ and $R^5$ together are a $3\alpha,5$-bond and $R^6$ is $C_{1-4}$-alkoxy; or, wherein $R^{11}$ is hydrogen or a readily-cleavable etherified hydroxy group of the formula R'O—C(R,R'')—O— in which R is hydrogen or $C_{1-4}$-alkyl and R' and R'' are $C_{1-4}$-alkyl or R' and R'' together are $C_{3-6}$-alkylene, $R^3$ is a readily cleavable etherified hydroxy group of the formula R'—C(R,R'')—O—, in which R, R' and R'' are as hereinbefore defined, and $R^5$ and $R^6$ together are a C—C bond.

2. A compound selected from the group consisting of:

(20S)-6β-methoxy-20-methyl-21-phenylsulphonyl-3α,5-cyclo-5α-pregnane, (20S)-20-methyl-21-phenylsulphonyl-3β-(tetrahydro-2H-pyran-2-yl)-oxy-pregn-5-ene, and (20S)-1α,3β-di-(tetrahydro-2H-pyran-2-yl)-oxy-20-methyl-21-phenylsulphonyl-pregn-5-ene.

3. A process for the manufacture of cholesterol derivatives of the formula

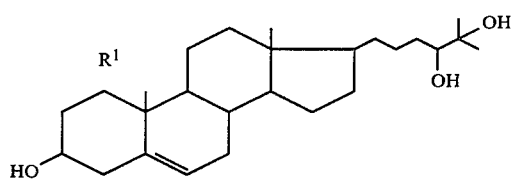

wherein

R$^1$ is hydrogen or hydroxy, which process comprises (a) reacting a pregnane derivative of the formula

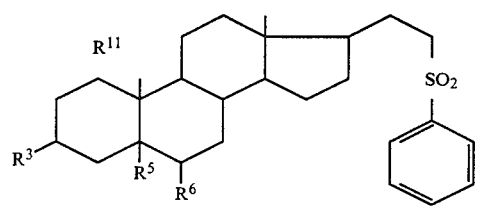

wherein R$^{11}$ is hydrogen, R$^3$ and R$^5$ together are a 3,5-bond and R$^6$ is C$_{1-4}$-alkoxy; or, R$^{11}$ is hydrogen or a readily cleavable etherified hydroxy group of the formula R'—C(R,R'')—O— in which R is hydrogen or —C$_{1-4}$-alkyl and R' and R'' are C$_{1-4}$-alkyl or R' and R'' together are C$_{3-6}$-alkylene, R$^3$ is a readily cleavable etherified group of the formula R'—C(R,R'')—O— wherein R, R' and R'' are as hereinbefore defined, and R$^5$ and R$^6$ together are a C—C bond, with a compound of the formula

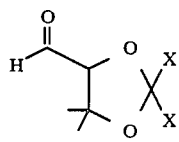

wherein X is hydrogen or methyl, (b) reductively eliminating the β-hydroxysulphonyl grouping from the resulting compound of the formula

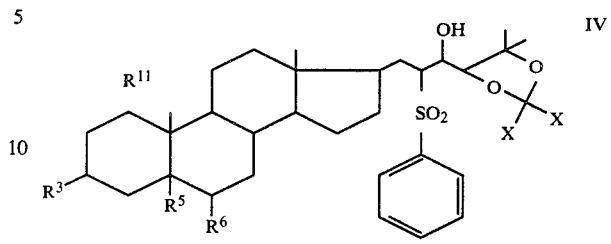

wherein X, R$^{11}$, R$^3$, R$^5$ and R$^6$ are as hereinbefore defined, (c) catalytically hydrogenating the resulting compound of the formula

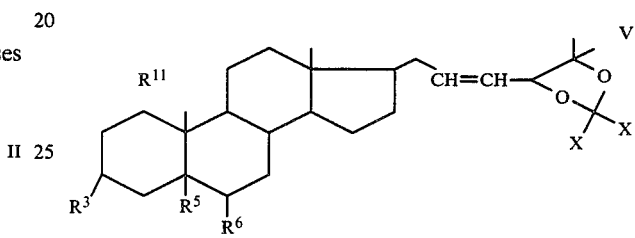

wherein X, R$^{11}$, R$^3$, R$^5$ and R$^6$ are as hereinbefore defined, and, (d) hydrolyzing the resulting compound of the formula

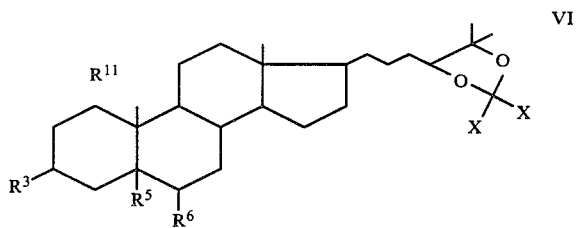

wherein X, R$^{11}$, R$^3$, R$^5$ and R$^6$ are as hereinbefore defined, to yield a compound of formula I.

4. The process according to claim 3 further comprising the step of resolving a resulting diastereomeric mixture of compounds of formula I.

5. A process in accordance with claim 3 for the manufacture of compounds of formula I having the 24R- or the 24S-configuration, said process employing an aldehyde of formula III which has either the R- or the S-configuration.

* * * * *

UNITED STATES PATENT AND TRADEMARK OFFICE
CERTIFICATE OF CORRECTION

PATENT NO. : 4,568,491
DATED : February 4, 1986
INVENTOR(S) : ANDOR FURST, LUDWIG LABLER, WERNER MEIER Page 1 of 4

It is certified that error appears in the above-identified patent and that said Letters Patent is hereby corrected as shown below:

The formule should appear as shown below:

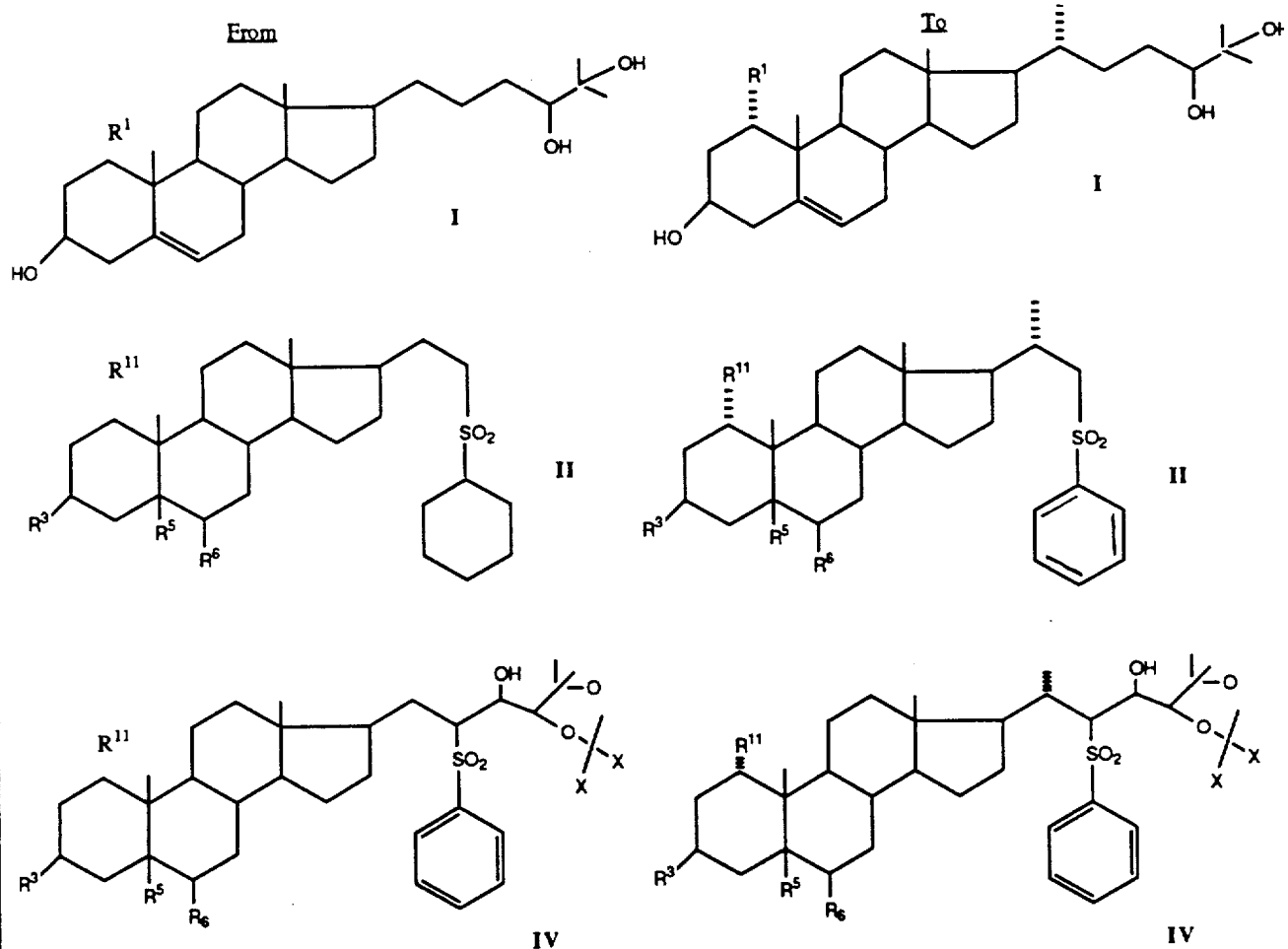

UNITED STATES PATENT AND TRADEMARK OFFICE
CERTIFICATE OF CORRECTION

PATENT NO. : 4,568,491
DATED : February 4, 1986
INVENTOR(S) : ANDOR FURST, LUDWIG LABLER, WERNER MEIER It is certified that error appears in the above-identified patent and that said Letters Patent is hereby corrected as shown below:

From

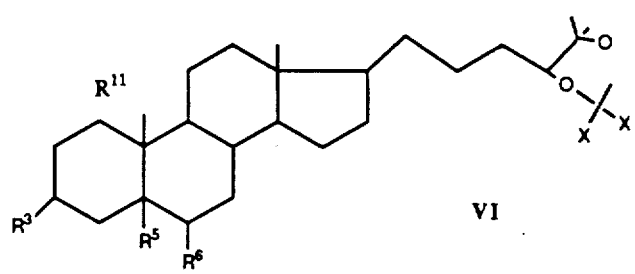

VI

To

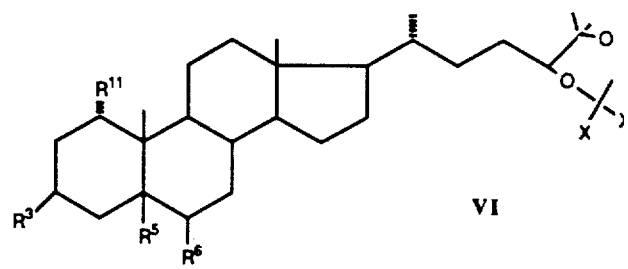

VI

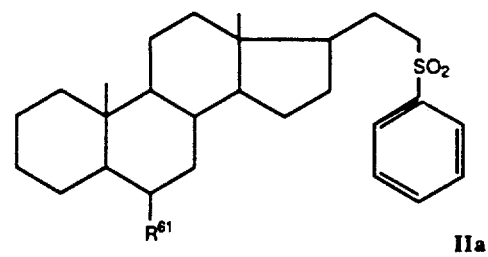

IIa

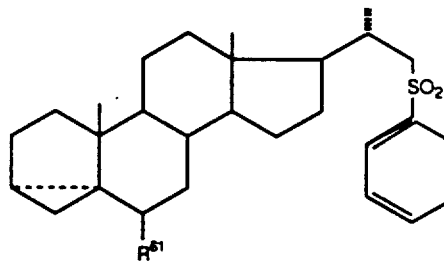

IIa

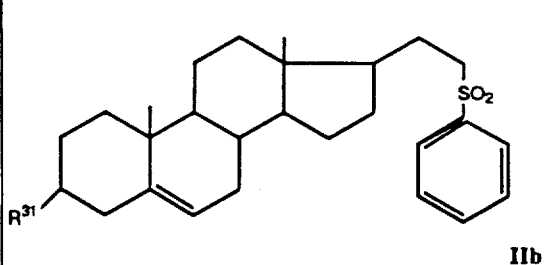

IIb

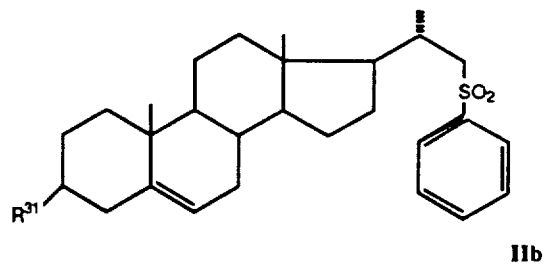

IIb

UNITED STATES PATENT AND TRADEMARK OFFICE
CERTIFICATE OF CORRECTION

PATENT NO. : 4,568,491
DATED : February 4, 1986
INVENTOR(S) : ANDOR FURST, LUDWIG LABLER, WERNER MEIER It is certified that error appears in the above-identified patent and that said Letters Patent is hereby corrected as shown below:

From

To

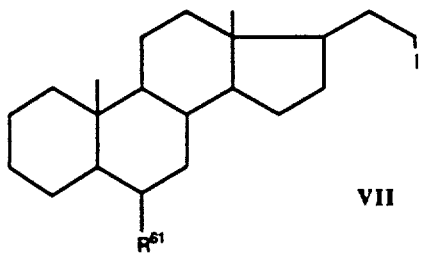

VII

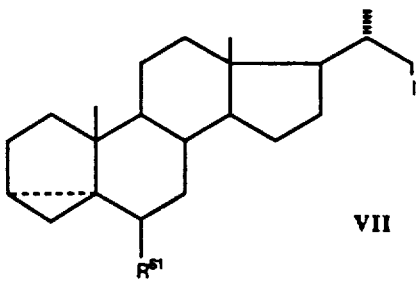

VII

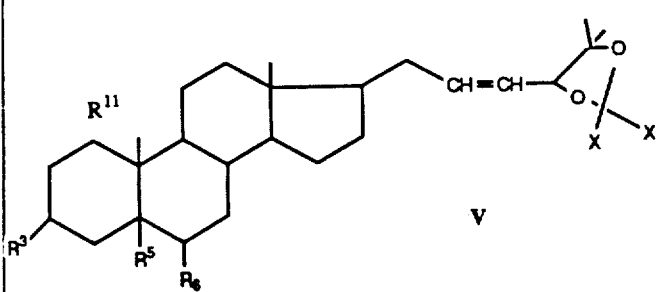

V

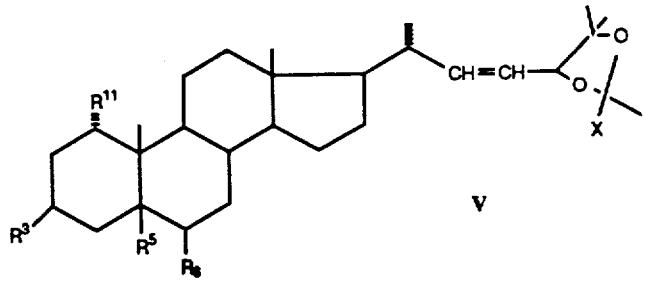

V

UNITED STATES PATENT AND TRADEMARK OFFICE
CERTIFICATE OF CORRECTION

PATENT NO. : 4,568,491

DATED : February 4, 1986

INVENTOR(S) : ANDOR FURST, LUDWIG LABLER, WERNER MEIER

It is certified that error appears in the above-identified patent and that said Letters Patent is hereby corrected as shown below:

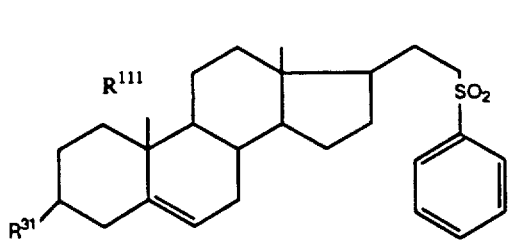

IIc

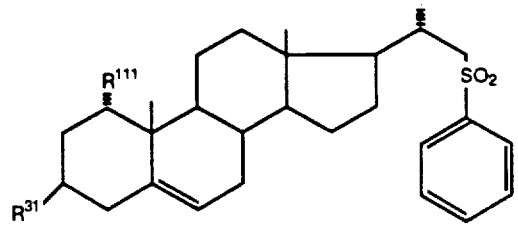

IIc

Signed and Sealed this

Twenty-fifth Day of October, 1988

Attest:

DONALD J. QUIGG

Attesting Officer

Commissioner of Patents and Trademarks